United States Patent [19]

Watatsuki et al.

[11] Patent Number: 4,740,609

[45] Date of Patent: * Apr. 26, 1988

[54] PHOSPHORIC ESTERS AND PROCESS FOR PREPARING SAME

[75] Inventors: Junya Watatsuki; Tohru Katoh, both of Wakayama; Tomihiro Kurosaki, Sennan, all of Japan

[73] Assignee: Kao Corporation, Tokyo, Japan

[*] Notice: The portion of the term of this patent subsequent to Apr. 5, 2005 has been disclaimed.

[21] Appl. No.: 878,681

[22] Filed: Jun. 26, 1986

[30] Foreign Application Priority Data

Jul. 31, 1985 [JP] Japan .................................. 60-169513

[51] Int. Cl.$^4$ .............................................. C07F 9/11
[52] U.S. Cl. ..................... 558/105; 558/177
[58] Field of Search ................................. 558/105, 177

[56] References Cited

U.S. PATENT DOCUMENTS

| | | | |
|---|---|---|---|
| 3,070,620 | 12/1962 | Gold ..................... | 558/179 |
| 4,215,064 | 7/1980 | Lindemann et al. ................. | 558/105 |
| 4,283,542 | 8/1981 | O'Lenick, Jr. et al. ............ | 558/166 |
| 4,623,743 | 11/1986 | Kurosaki et al. .................... | 558/169 |

*Primary Examiner*—Anton H. Sutto
*Attorney, Agent, or Firm*—Oblon, Fisher, Spivak, McClelland & Maier

[57] ABSTRACT

Novel phosphoric esters of the general formula

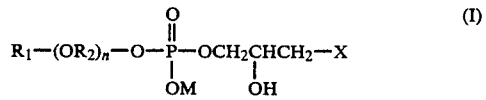

in which X represents a halogen, $R_1$ represents a linear or branched alkyl, fluoroalkyl or alkenyl group having from 1 to 36 carbon atoms, or a phenyl group substituted with a linear or branched alkyl group having from 1 to 15 carbon atoms, $R_2$ represents an alkylene group having 2 or 3 carbon atoms, n is a value of from 0 to 30, and M represents a hydrogen atom, alkali metal, alkaline earth metal, ammonium, or an alkylamine or alkanolamine salt are prepared by reacting a salt of a phosphoric monoester of the general formula (II)

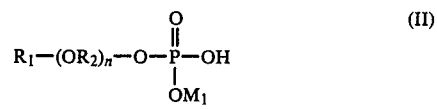

in which $R_1$, $R_2$ and n have, respectively, the same meanings as defined above, and $M_1$ represents an alkali metal, with an epihalohydrin of the general formula (III)

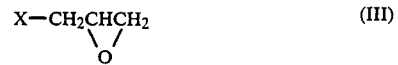

in which X has the same meaning as defined above, and optionally, converting the resulting product into a free acid or a different salt.

The phosphoric esters are reacted with a trialkylamine to readily obtain phospholipid simulants having a quaternary ammonium salt in a molecule thereof. When an alkali is acted on the phosphoric esters, the dehydrohalogenation reaction takes place and the esters are converted into a phosphoric ester having a polymerizable group.

3 Claims, 1 Drawing Sheet

PHOSPHORIC ESTERS AND PROCESS FOR PREPARING SAME

BACKGROUND OF THE INVENTION (1) Field of the Invention

This invention relates to novel phosphoric esters and more particularly, to phosphoric esters of the following general formula (I), and to a process for preparing same,

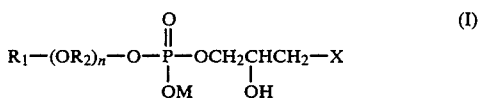

in which X represents a halogen, $R_1$ represents a linear or branched alkyl, fluoroalkyl or alkenyl group having from 1 to 36 carbon atoms, or a phenyl group substituted with a linear or branched alkyl group having from 1 to 15 carbon atoms, $R_2$ represents an alkylene group having 2 or 3 carbon atoms, n is a value of from 0 to 30, and M represents a hydrogen atom, alkali metal, alkaline earth metal, ammonium, or an alkylamine or alkanolamine salt.

(2) Description of the Prior Art

Phosphoric esters have been widely utilized in various fields of detergents, fiber treatments, emulsifiers, rust preventives, liquid ion exchangers and medicines. Among phosphoric esters, alkali metal salts of phosphoric monoesters are far superior to other phosphoric esters, such as alkali metal salts of phosphoric diesters, with respect to surface activity and the like properties. For instance, alkali metal salts or alkanolamine salts of monoesters between longchain alkyl alcohols and phosphoric acid are soluble in water. The aqueous solutions of these salts have very good foaming ability and detergency. In contrast, phosphoric diester salts are sparingly soluble in water and show little foaming ability but a foam-suppressing property.

On the other hand, currently employed detergents include alkylsulfates, alklybenzenesulfonates, alpha-olefinsulfonates and the like. Most of these surface active agents undergo skin irritation. In recent years, phosphoric monoester salts have been used as less irritative surface active agents.

As is well known in the art, a living body contains a number of surface active agents of the phosphoric ester type, which are called phospholipids, such as lecithin, phosphatidyl serine and have a quaernary ammonium in one molecule thereof. These phospholipids exhibit surface activity, emulsifiability, and physiological characteristics and are thus utilized in various fields. Accordingly, it is expected that substances having structures similar to those of phospholipids are less irritative against a living body than monoalkyl phosphoric ester salts. Therefore, a variety of phospholipid-like substances have been synthesized. However, the synthetic processes require, in most cases, a number of reaction steps and intended products are thus obtained only in low yield [see, for example, E. Baer et al, J. Amer. Chem. Soc., 72, 942 (1950)].

Some of the present inventors have prepared, by a simple procedure, and proposed (in Japanese patent application No. 59-39042) compounds having a quaternary ammonium salt in one molecule thereof and represented by the following formula (IV)

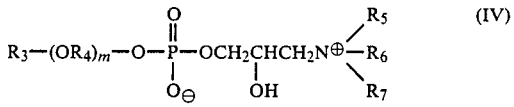

in which $R_3$ represents a saturated or unsaturated, linear or branched hydrocarbon group having from 8 to 32 carbon atoms with or without a substituent, $R_5$, $R_6$ and $R_7$ are the same or different and are a saturated or unsaturated hydrocarbon group having from 1 to 4 carbon atoms, $R_4$ represents an alkylene group having 2 or 3 carbon atoms, and m is an integer of from 0 to 50. This compound is readily prepared according to the following reaction formula in which a glycidyltrialkylammonium salt of the formula (VI) is reacted with a monoalkali metal salt of a monoalkyl phosphate (V). More specifically, dodecyl 2-hydroxy-3-N,N,N-trimethylammonio-propyl phosphate (in compound (IV), $R_3$ = $C_{12}H_{25}$, $R_5$=$R_6$=$R_7$=$CH_3$, and m=0) has found to have good detergency and to be very low in irritation against a living body.

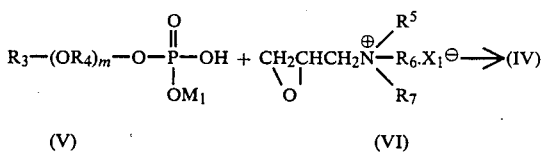

in which $M_1$ represents an alkali metal, $X_1$ represents an anion, and $R_3$, $R_4$, $R_5$, $R_6$, $R_7$ and m have, respectively, the same meanings as defined before.

However, glycidyltrimethylammonium chloride is only one glycidyltrialkylammonium salt (VI) which is industrially available. Thus, it was difficult to industrially obtain compounds having various alkylammonio groups.

In the field of polymer science, studies have been made on the addition or modification of various functions to polymeric materials. In on such study, the impartment of functional properties of phosphoric acid groups or phosphoric esters, such as surface activity, chelating property, antistaticity and the like, to polymeric compounds have been extensively made in recent years.

The methods of introducing phosphorus compounds to polymeric compounds may be divided into the following three groups.

(1) Phosphorus compounds are blended with polymeric compounds.

(2) Reactive functional groups of polymeric compounds, e.g. hydroxyl groups, are phosphorilized.

(3) Phosphorus compounds serving as monomers are polymerized.

However, the method (1) is disadvantageous in that phosphorus compounds used are apt to separate from polymer compounds such as by exudation. The method (2) has the drawback that limitation is placed on the phosphorizing agent and phosphorization cannot be effected as desired. Accordingly, there is a demand of development of phosphorus compounds, used as monomers in the method (3), e.g. phosphoric esters having polymerizable groups.

Moreover, in the field of polymer films which are one of applications of polymers, studies have been extensively made on artificial films or membranes having functions of a living membrane, e.g. formation of a section and a selective transport function for a substance. These films or membranes are intended to be applied to diverse fields of engineering, medical science, pharmacy and the like. The difference between a living membrane and an artificial polymer membrane resides in that the living membrane has such a structure that the molecules are systematically oriented and, for example, a bimolecular layer structure is formed. This orientation is ascribed to the physical properties of phospholipid molecules, which are constituents of a living membrane, or the properties of self-assembling and organizing the molecules inherent to so-called amphiphilic compounds having both hydrophobic and hydrophilic groups. Accordingly, when a monomer for use as a material for membranes is taken into account, attention has been paid, more or less, to not only to chemical properties of the monomer, but also physical properties, such as surface activity and self-organizability. To this end, a number of phosphoric ester monomers having such properties as surface activity, affinity for living bodies and the like, have been synthesized, with a difficulty in industrially obtaining such monomers.

SUMMARY OF THE INVENTION

Under these circumstances in the art, the present inventors made intensive studies. As a result, it was found that phosphoric monoesters with high purity had good surface activity and monoalkali salts of phosphoric monoesters were soluble in water. Moreover, it was also found that monoalkali metal salts of phosphoric monoesters and epihalohydrins were reacted in high selectivity in an aqueous solution system, so that functional groups could be introduced into the phosphoric esters in high selectivity and intended compounds could be readily obtained in high purity. In addition, when the resultant compounds were reacted with various trialkylamines, there were obtained compounds which could be readily converted into compounds of the aforeindicated formula (IV). The converted compounds were able to form epoxy rings by the action of alkalis and were readily converted into phosphoric ester monomers. The present invention is accomplished based on the above findings.

Therefore, the present invention provides novel phosphoric esters of the formula (I) and also a novel process for preparing phosphoric esters of the formula (I).

BRIEF DESCRIPTION OF THE DRAWING

The sole figure is an IR absorption spectrum of sodium dodecyl 2-hydroxy-3-chloropropylphosphate obtained in Example 1.

DETAILED DESCRIPTION OF THE INVENTION AND PREFERRED EMBODIMENTS

Figure 1:
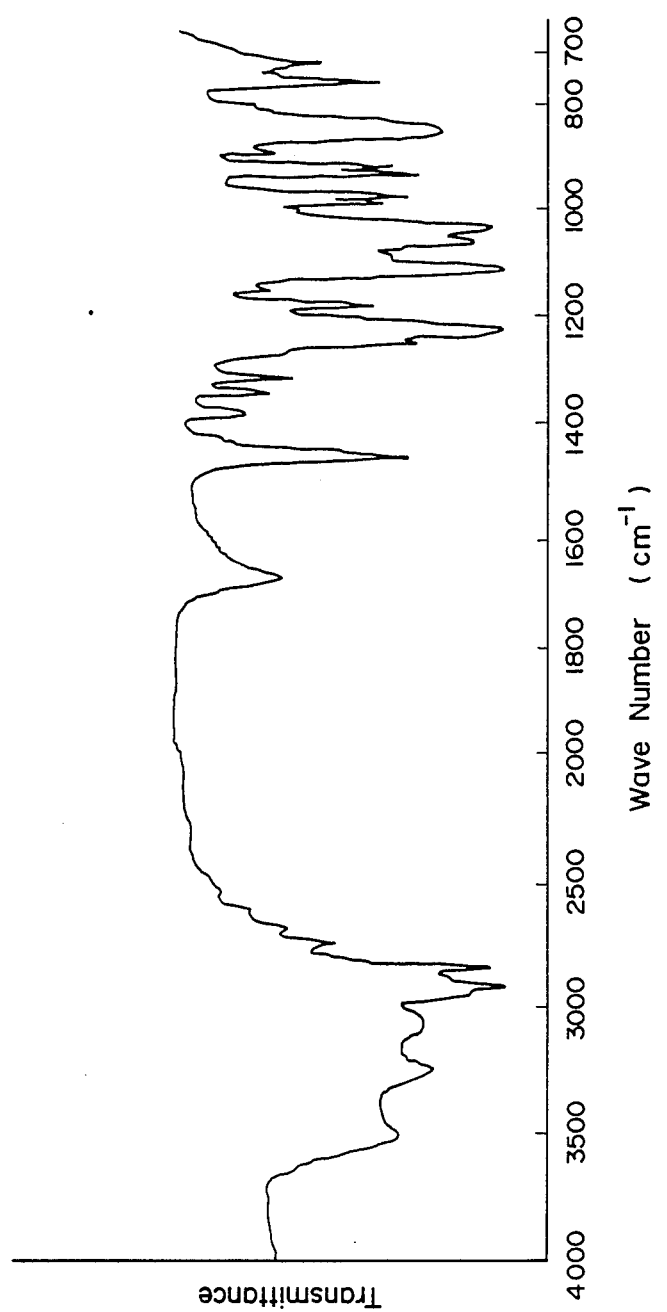

In the phosphoric esters of the formula (I), the linear or branched alkyl, fluoroalkyl or alkenyl groups represented by $R^1$ and having from 1 to 36 carbon atoms include, for example, methyl, ethyl, butyl, octyl, decyl, dodecyl, tetradecyl, hexadecyl, octadecyl, docosyl, tetracosyl, triacontyl, 2-ethylhexyl, 2-octyldodecyl, 2-dodecylhexadecyl, 2-tetradecyloctadecyl, emery-isostearyl, tridecafluorooctyl, pentadecafluorodecyl, heneicosafluorododecyl, 2-tridecafluorohexyltridecafluorodecyl, octenyl, decenyl, dodecenyl, tetradecenyl, hexadecenyl, octadecenyl, docosenyl, tetracosenyl, triacontenyl, nonylphenyl, and the like. Of these, the groups having from 8 to 36 carbon atoms are preferred in view of surface activity and self-organizability.

The phosphoric esters (I) of the invention are prepared by reaction between salts of phosphoric monoesters of the general formula (II)

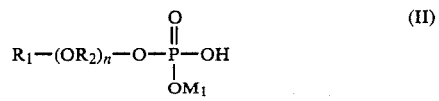

in which $R_1$, $R_2$, $M_1$ and n have, respectively, the same meanings as defined before, and epihalohydrins of the general formula (III)

in which X represents a halogen. If necessary, the esters may be converted into free acids or other salts.

The phosphoric monoesters used to prepare the monoalkali metal salts of phosphoric monoesters of the general formula (II) can be prepared by reaction between corresponding organic hydroxy compounds and phosphorylating agents such as phosphorus pentaoxide, phosphorus oxychloride, polyphosphoric acid and the like. Any monoesters may be used as obtained above, and the phosphoric monoester salts (II) for use in the preparation of the phosphoric esters (I) of the invention should preferably have high purity. When phosphorus pentaoxide or phosphorus oxychloride is used as the phosphorylating agent, phosphoric diesters are secondarily produced. The diesters will lower or lose the surface activity and self-organizability of the phosphoric monoester and will lower the purity of intended compounds obtained by subsequent reaction with epoxy compounds. This makes it difficult to obtain a highly pure intended product by purification. Orthophosphoric acid, which are secondarily produced on use of polyphosphoric acid as the phosphorylating agent, will lower the yield of intended products obtained by reaction with epoxy compounds. This leads to a difficulty in obtaining highly pure intended products. Accordingly, the purity of the phosphoric monoester salts (II) should be preferably not less than 90 wt %. A process of industrially producing such highly pure phosphoric monoesters have been proposed by some of the present inventors (Japanese patent application No. 59-138829). Also, some of the present inventors have proposed a method of removing orthophosphoric acid from a mixture of monopolyoxyethylene or polyoxypropyleneglycol alkylphosphate and orthophosphoric acid (Japanese patent application No. 59-251409).

In the above reaction, the epihalohydrin (III) is used in an amount of from 1 to 10 moles, preferably from 3 to 5 moles, per mole of the monoalkali metal salt of a phosphoric monoester (II).

If the phosphoric monoester is used for the reaction without conversion into monoalkali metal salts, there are produced, aside from intended compounds, byproducts of phosphoric triesters obtained by reaction of further one mole of the compound of the formula (III), thus lowering the yield of the intended product. Accordingly, in order to carry out the above reaction, the phosphoric monoesters should preferably be used in the form of the monoalkali metal salts (II).

The solvents used for the reaction are preferably inert, polar solvents including, for example, water, methyl alcohol, ethyl alcohol and the like, of which water is preferred. The use of water as the solvent is very favorable in the industrial production from the standpoint of safety.

The reaction temperature is in the range of from 30° to 100° C., preferably from 50° to 90° C.

The resulting reaction solution contains, aside from a compound of the formula (I), an unreacted compound of the formula (III) or a hydrolyzate of the compound of the formula (III). The reaction product may be used as it is, depending on the purpose, and may be purified to obtain a highly pure product. For instance, with sodium dodecyl 2-hydroxy-3-chloropropylphosphate (in the formula (I), $R_1=C_{12}H_{25}$, $X=Cl$, $M=Na$), epichlorohydrin is reacted with sodium dodecyl phosphate in the form of an aqueous solution. Thereafter, water is distilled off, or an electrolyte such as sodium chloride, potassium chloride or the like is added to the reaction solution to a saturation. The organic matters are extracted with an organic solvent such as ethyl ether, after which the ethyl ether is distilled off to separate from water. Acetone is added so as to precipitate sodium dodecyl 2-hydroxy-3-chloropropylphosphate, whereupon epichlorohydrin and a hydrolyzate thereof, which are soluble in acetone, can be separated from the product. Thus, the product of high purity can be obtained. Alternatively, other purification methods may be used. In one such method, the reaction solution is rendered acidic, and the organic matters are extracted with an organic solvent such as ethyl ether, followed by well washing with water to remove the hydrolyzate of epichlorohydrin. Thereafter, dodecyl 2-hydroxy-3-chloropropylphosphate is extracted from the organic phase with an aqueous alkaline solution. The aqueous solution is rendered acidic and extracted with an organic solvent such as ethyl ether, followed by removal of the ethyl ether by distillation to obtain dodecyl 2-hydroxy-3-chloropropylphosphate. If desired, the phosphate may be used after neutralization with a base such as ammonium, an alkylamine, an alkanolamine or the like.

Depending on the reaction conditions, there may be produced, aside from the phosphoric esters of the general formula (I) of the invention, a small amount of a phosphoric ester of the following general formula (VII)

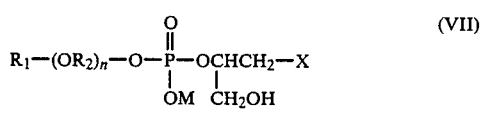

(VII)

in which M represents a hydrogen atom, alkali metal, alkaline earth metal, ammonium, or alkylamine or alkanolamine salt, X, $R_1$, $R_2$ and n have the same meanings as defined before, respectively.

When the phosphoric esters (I) of the invention are reacted with various trialkylamines according to the following reaction formula, there are readily obtained phospholipid simulants (VIII) having a quaternary ammonium salt in the molecule thereof, which have heretofore been difficult to obtain industrially.

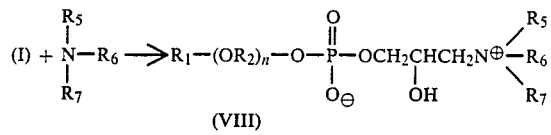

(VIII)

in which $R_1$, $R_2$, $R_5$, $R_6$, $R_7$ and n have the same meanings as defined before, respectively.

When an alkali is acted on the phosphoric ester (I) of the invention, dehydrohalogenation reaction takes place readily, thus converting the ester (I) into a phosphoric ester of the formula (IX) having a polymerizable group.

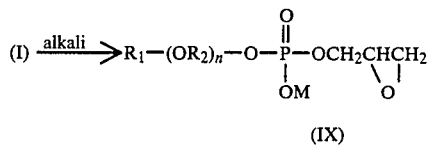

(IX)

in which $R_1$, $R_2$, M and n have the same meanings as defined before, respectively.

The present invention is described by way of examples and test examples.

EXAMPLE 1

Two hundred grams of monododecyl phosphate with a purity of 97% [0.73 mol, AV1 (amount by mg of KOH required for neutralizing 1 g of the phosphoric monoester sample to a first equivalent point)=210.3, AV2 (amount by mg of KOH required for neutralizing 1 g of the phosphoric monoester sample to a second equivalent point)=420.8] was charged into a reactor, to which 750 ml of an aqueous 1N sodium hydroxide solution, followed by agitation and raising the temperature to 80° C. to obtain a uniform solution. The acid value of the reaction solution (amount by mg of KOH required for neutralizing 1 g of the sample) was found to be 42.9. Subsequently, while the reaction system was maintained at 80° C., 347 g (3.75 mol) of epichlorohydrin was gradually added and agitated at the temperature for 4 hours. The acid value of the reaction system was almost zero, revealing that the reaction completed. Thereafter, the reaction solution was freeze-dried and 1000 ml of acetone was added to the resulting non-volatile liquid residue, followed by being allowed to stand at 5° C. One day after, the resulting crystals were collected and recrystallized from acetone to obtain 193 g (yield 69.4%) of white crystals of sodium dodecyl 2-hydroxy-3-chloropropylphosphate.

$^1$H NMR:

δ 0.8 ppm (t, 3H, —P—OCH$_2$(CH$_2$)$_{10}$C$\underline{H}_3$)

δ 1.3 ppm (broad s, 20H, —P—OCH$_2$(C$\underline{H}_2$)$_{10}$CH$_3$)

δ 3.4–4.1 ppm (broad, 7H, Cl—C$\underline{H}_2$C$\underline{H}$C$\underline{H}_2$OPOC$\underline{H}_2$—)
                                                   O$\underline{H}$ $^{13}$C NMR

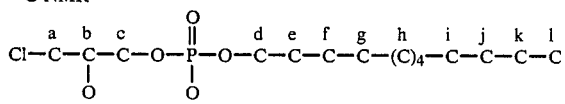

δ (ppm) l; 14.6, k; 23.5, f; 26.7, g, i; 30.4,
h; 30.7, e; 31.6, j; 32.8, a; 45.2, c;
67.0, b; 70.7, d; 72.3

-continued

Standard sample: $Si(CH_3)_3-C_3H_6-SO_3Na$
IR (KBr): see FIG.
Elementary analysis:

|  | C(%) | H(%) | P(%) | Na(%) | Cl(%) |
|---|---|---|---|---|---|
| Found | 47.08 | 8.15 | 8.0 | 6.3 | 9.45 |
| Calculated | 47.31 | 8.21 | 8.1 | 6.0 | 9.31 |

TEST EXAMPLE 1

Fifty grams (0.13 mol) of sodium dodecyl 2-hydroxy-3-chloropropylphosphate obtained in Example 1 was charged into a reactor and reacted with 28.8 g (0.13 mol) of dodecyldimethylamine in a mixed solvent of water and ethanol. The analysis by high pressure liquid chromatography (HPLC) revealed that the peaks of the starting material disappeared and peaks of a new product appeared. The product was collected from HPLC and the solvent was distilled off under reduced pressure to obtain sodium dodecyl 2-hydroxy-3-N-dodecyl-N,N-dimethylammoniopropylphosphate.

TEST EXAMPLE 2

Ten grams (0.026 mol) of sodium dodecyl 2-hydroxy-3-chloropropylphosphate obtained in Example 1 was charged into a reactor, to which 25 g of water was added for dissolution. While the reactor was cooled in ice, 6 g of an aqueous solution containing 1.0 g of sodium hydroxide was added under agitation and agitated for 1.5 hours. The reaction solution was freeze-dried. Upon confirmation by $^1$H-NMR, the starting material was scarcely found but sodium dodecyl glycidylphosphate was formed.

EXAMPLE 2

Similar to Example 1, 200 g of monooctadecyl phosphate (0.55 mol, AV1=160.7, AV2=321.5) having a purity of 97% was dissolved in 573 ml of an aqueous 1N potassium hydroxide solution at 55° C., whereupon the acid value was 40.3, followed by gradual addition of 265 g (2.86 mol) of epichlorohydrin and agitation at the temperature for 20 hours. At this time, the acid value of the reaction system was almost zero, revealing that the reaction rate was almost 100%. The reaction solution was cooled down to room temperature and transferred to a dropping funnel. Concentrated hydrochloric acid was added to adjust the pH to 1, followed by extraction twice with each 400 ml of ethyl ether. The organic phases were combined and washed five times with each 200 ml of water and then twice with each 500 ml of an 1N potassium hydroxide solution. The aqueous phase was washed once with 400 ml of ethyl ether, to which concentrated hydrochloric acid was added so as to adjust the pH to 1, followed by extraction twice with each 400 ml of ethyl ether. The ethyl ether was distilled off under reduced pressure to obtain 198 g (yield 81.2%) of octadecyl 2-hydroxy-3-chloropropylphosphate.

| | Elementary analysis: | | | |
|---|---|---|---|---|
| | C (%) | H (%) | P (%) | Cl (%) |
| Found | 56.77 | 9.84 | 7.0 | 8.20 |
| Calculated | 56.94 | 10.01 | 7.0 | 8.00 |

EXAMPLE 3

Twenty grams of mono2-hexyldecyl phosphate (0.057 mol, AV1=167.2, AV2=329.8) having a purity of 92% was dispersed in 59.6 ml of an aqueous 1N sodium hydroxide solution (with an acid value of the reaction system of 39.5). To the dispersion was gradually added 16.5 g (0.178 mol) of epichlorohydrin at 80° C., at which the system was agitated for 8 hours. The acid value of the reaction system was almost zero and thus, the reaction rate of the phosphoric monester was almost 100%. The reaction solution was analysed by HPLC, revealing peaks of a hydrolyzate of epichlorohydrin and a new product. The production was collected from the reaction mixture by HPLC and the solvent was distilled off under reduced pressure to obtain 20.5 g (yield 82.3%) of sodium 2-hexyldecyl 2-hydroxy-3-chloropropylphosphate.

| | Elementary analysis: | | | | |
|---|---|---|---|---|---|
| | C (%) | H (%) | P (%) | Na (%) | Cl (%) |
| Found | 52.05 | 8.79 | 7.1 | 5.8 | 8.37 |
| Calculated | 52.23 | 9.00 | 7.1 | 5.3 | 8.11 |

EXAMPLE 4

Twenty grams of mono2-decyltetradecyl phosphate (0.043 mol, AV1=134.2, AV2=267.1) having a purity of 94% was charged into a reactor, to which 47.8 ml of an aqueous 1N potassium hydroxide was added and agitated, followed by raising the temperature to 70° C. to obtain a uniform dispersion whose acid value was 37.9. Subsequently, while keeping the reaction system at 70° C., 13.2 g (0.143 mol) of epichlorohydrin was gradually dropped into the system, followed by agitation at the temperature for 20 hours. The acid value of the reaction system was almost zero, thus revealing that the reaction rate of the phosphoric monoester was almost 100%. The reaction product was collected by HPLC and the solvent was distilled off under reduced pressure to obtain 19.8 g (yield 81.5%) potassium 2-decyltetradecyl 2-hydroxy-3-chloropropylphosphate.

| | Elementary analysis: | | | | |
|---|---|---|---|---|---|
| | C (%) | H (%) | P (%) | K (%) | Cl (%) |
| Found | 52.25 | 8.88 | 6.3 | 8.5 | 7.66 |
| Calculated | 52.43 | 9.01 | 6.4 | 8.1 | 7.37 |

The analysis by HPLC revealed that the purity was 98 to 99%.

EXAMPLE 5

Twenty grams of monobutyl phosphate (0.13 mol, AV1=360.6, AV2=721.3) having a purity of 99% was charged into a reactor, to which 129 ml of an aqueous 1N sodium hydroxide solution was added. The system was agitated for dissolution at 70° C., whereupon the system had an acid value of 46.7. Subsequently, while keeping the reaction system at 70° C., 59.2 g (0.64 mol) of epichlorohydrin was gradually dropped i nto the system, followed by agitation at the temperature for 20 hours. The reaction system had an acid value of almost zero, revealing that the reaction rate of the phosphoric monoester was almost 100%. The reaction product was collected by HPLC and the solvent was distilled off under reduced pressure to obtain 30.2 g (yield 86.5%) of sodium butyl 2-hydroxy-3-chloropropylphosphate.

|  | Elementary analysis: | | | | |
|---|---|---|---|---|---|
|  | C (%) | H (%) | P (%) | Na (%) | Cl (%) |
| Found | 31.14 | 5.38 | 11.2 | 8.9 | 13.55 |
| Calculated | 31.30 | 5.63 | 11.5 | 8.6 | 13.20 |

The analysis by HPLC revealed that the purity was 98 to 99%.

EXAMPLE 6

Twenty grams of monotrioxyethyleneglycol dodecyl phosphate (0.049 mol, AV1=142.8, AV2=288.2) having a purity of 98% was charged into a reactor, to which 50.9 ml of an aqueous 1N potassium hydroxide solution was added. The system was agitated for dissolution at 80° C., whereupon the system had an acid value of 39.5. Subsequently, while keeping the reaction system at 80° C., 22.7 g (0.25 mol) of epichlorohydrin was gradually dropped into the system, followed by agitation at the temperature for 6 hours. At this stage, the reaction system had an acid value of almost zero, revealing that the reaction rate of the phosphoric monoester was almost 100%. The reaction product was collected by HPLC and the solvent was distilled off under reduced pressure to obtain 19.3 g (yield 74.5%) of potassium trioxyethyleneglycol dodecyl 2-hydroxy-3-chloropropylphosphate.

|  | Elementary analysis: | | | | |
|---|---|---|---|---|---|
|  | C (%) | H (%) | P (%) | K (%) | Cl (%) |
| Found | 47.39 | 7.95 | 5.9 | 7.3 | 6.99 |
| Calculated | 47.68 | 8.14 | 5.9 | 7.4 | 6.72 |

The analysis by HPLC revealed that the purity was 98 to 99%.

EXAMPLE 7

Twenty grams of mononoylphenyl phosphate (0.060 mol, AV1=168.2, AV2=338.2) having a purity of 0% was charged into a reactor, to which 60.0 ml of an aqueous 1N potassium hydroxide solution was added, followed by uniform dispersion under agitation at 80° C., whereupon the system had an acid value of 42.3. Subsequently, while keeping the reaction system at 80° C., 7.8 g (0.30 mol) of epichlorohydrin was gradually dropped into the system, followed by agitation at the temperature for 6 hours. At this stage, the reaction system had an acid value of almost zero, revealing that the reaction rate of the phosphoric monoester was almost 100%. The reaction product was collected by HPLC and the solvent was distilled off under reduced pressure to obtain 18.1 g (yield 70.0%) of potassium nonylphenyl 2-hydroxy-3-chloropropylphosphate.

|  | Elementary analysis: | | | | |
|---|---|---|---|---|---|
|  | C (%) | H (%) | P (%) | K (%) | Cl (%) |
| Found | 49.83 | 6.56 | 7.3 | 9.0 | 8.59 |
| Calculated | 50.17 | 6.78 | 7.2 | 9.1 | 8.23 |

The analysis by HPLC revealed that the purity was 98 to 99%.

EXAMPLE 8

Twenty grams of monooctadecenyl phosphate (0.052 mol, AV1=165.0, AV2=323.2) having a purity of 90% was charged into a reactor, to which 58.8 ml of an aqueous 1N potassium hydroxrde solution was added, followed by uniform dispersion under agitation at 80° C., whereupon the system had an acid value of 40.2. Subsequently, while keeping the reaction system at 80° C., 24.1 g (0.26 mol) of epichlorohydrin was gradually dropped into the system, follwed by agitation at the temperature for 6 hours. At this stage, the reaction system had an acid value of almost zero, revealing that the reaction rate of the phosphoric monoester was almost 100%. The reaction product was collected by HPLC and the solvent was distilled off under reduced pressure to obtain 16.9 g (yield 67.8%) of potassium octadecenyl 2-hydroxy-3-chloropropylphosphate.

|  | Elementary analysis: | | | | |
|---|---|---|---|---|---|
|  | C (%) | H (%) | P (%) | K (%) | Cl (%) |
| Found | 52.08 | 8.52 | 6.5 | 8.1 | 7.63 |
| Calculated | 52.65 | 8.63 | 6.5 | 8.2 | 7.40 |

The analysis by HPLC revealed that the purity was 98 to 99%.

What is claimed is:

1. A phosphoric ester of the general formula (I)

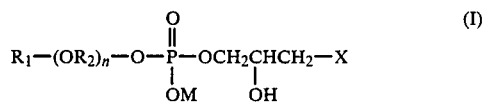

in which X represents a halogen, $R_1$ represents a linear or branched alkyl, fluoroalkyl or alkenyl group having from 1 to 36 carbon atoms, or a phenyl group substituted with a linear or branched alkyl group having from 1 to 15 carbon atoms, $R_2$ represents an alkylene group having 2 or 3 carbon atoms, n is a value of from 0 to 30, and M represents a hydrogen atom, alkali metal, alkaline earth metal, ammonium, or an alkylamine or alkanolamine salt.

2. A process for preparing a phosphoric ester of the general formula (I)

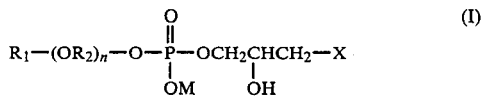

in which X represents a halogen, $R_1$ represents a linear or branched alkyl, fluoralkyl or alkenyl group having from 1 to 36 carbon atoms, or a phenyl group substituted with a linear or branched alkyl group having from 1 to 15 carbon atoms, $R_2$ represents an alkylene group having 2 or 3 carhbon atoms, n is a value of from 0 to 30, and M represents a hydrogen atom, alkali metal, alkaline earth metal, ammonium, or an alkylamine or alkanolamine salt, which comprises reacting a salt of a phosphoric monoester of the general formula (II)

$$R_1-(OR_2)_n-O-\overset{\overset{O}{\|}}{\underset{OM}{P}}-OH \qquad (II)$$

in which $R_1$, $R_2$ and n have, respectively, the same meanings as defined above, and $M_1$ represents an alkali metal, with an epihalohydrin of the general formula (III)

$$X-CH_2\overset{}{\underset{O}{CHCH_2}} \qquad (III)$$

in which X has the same meaning as defined above, wherein said reacting is carried out at a temperature of from 30° to 100° C. and the molar ratio of the phosphoric monoester to the epihalohydrin is 1:(3-50).

3. A process according to claim 2, which further comprises converting the product into a free acid or a different salt.

* * * * *